United States Patent [19]

Lowery et al.

[11] 4,394,323

[45] Jul. 19, 1983

[54] PRODUCTION OF ANTIMONY ORGANOPHOSPHORODITHIOATES

[75] Inventors: Richard E. Lowery, Bartlesville, Okla.; Bruce W. Gordon; Barry N. Steger, both of Borger, Tex.

[73] Assignee: Phillips Petroleum Company, Bartlesville, Okla.

[21] Appl. No.: 250,964

[22] Filed: Apr. 1, 1981

[51] Int. Cl.$^3$ .............................................. C07F 9/90
[52] U.S. Cl. .................................................. 260/446
[58] Field of Search ........................................ 260/446

[56] References Cited

U.S. PATENT DOCUMENTS

| | | | |
|---|---|---|---|
| 2,540,084 | 2/1951 | Asseff | 260/429 |
| 3,369,183 | 8/1968 | Brasch | 260/429 |
| 3,471,540 | 10/1969 | Walters | 260/429.9 |
| 4,025,458 | 5/1977 | McKay | 260/446 X |
| 4,031,002 | 6/1977 | McKay | 260/446 X |
| 4,166,806 | 9/1979 | McKay et al. | 260/446 X |
| 4,167,471 | 9/1979 | Bertus et al. | 260/446 X |
| 4,207,204 | 6/1980 | McKay et al. | 260/446 X |
| 4,209,453 | 6/1980 | Bertus et al. | 260/446 |

*Primary Examiner*—Helen M. S. Sneed

[57] ABSTRACT

The efficiency of salt-forming reactions between antimony compounds and hydrocarbylphosphorodithioic acids is improved by adding the antimony compounds in small increments.

4 Claims, No Drawings

PRODUCTION OF ANTIMONY ORGANOPHOSPHORODITHIOATES

BACKGROUND

In the catalytic cracking of hydrocarbons, metal contaminants are passivated by adding to the catalysts certain antimony compounds. Until now, one widely used group of compounds has been both difficult and expensive to prepare, due to the time-consuming filtration operations needed to remove by-products and unreacted reagents.

INVENTION

It has been discovered that the production and preparation of antimony salts of dihydrocarbylphosphorodithioic acids can be carried out more efficiently by adding the antimony reagent incrementally to the acids.

In one embodiment, antimony tris(di-n-propyl phosphorodithioate) is made by adding a stoichiometric excess of di-n-propylphosphorodithioic acid to antimony trioxide. The reaction is then completed by adding small increments of antimony oxide. Any excess oxide is removed by filtering the final solution.

OBJECTS OF THE INVENTION

It is an object of the invention to produce antimony organophosphorodithioates more efficiently.

It is a further object of the invention to minimize the handling and storage requirements of certain antimony salts.

It is another object of the invention to prepare antimony-containing passivators with minimal waste of antimony reagents.

It is yet another object of the invention to provide a method by which the number and duration of filtration steps needed to separate antimony-containing passivators is lessened.

It is yet another object of the invention to provide a method by which the number and duration of filtration steps needed to separate antimony-containing passivators is lessened.

ADVANTAGES

The process of the invention has several advantages over known processes of producing antimony salts. Among its principal advantages is the fact that the ease of filtration—i.e., the filtration rate—of the reaction mixture is dramatically improved. When the addition of the antimony reagent, e.g., antimony oxide, to the acid intermediate has been carried out in one step—i.e., all of the antimony oxide is added to the acid at once—it has been found that several days are required to filter the product to remove impurities; even which the assistance of conventional filter aids, such as diatomaceous earth. But when, in accordance with the instant invention, some or all of the antimony reagent is added in small increments, the complete neutralization of the acid is more easily detected, e.g., by color changes, and the impurities in the product can be filtered out in a matter of minutes.

Because of the ease with which the antimony salts are filtered, overall batch times can be cut in half, the number of filter elements needed is reduced, and the amount of antimony reagent needed for the reaction is decreased.

DESCRIPTION OF THE INVENTION

The antimony salts produced in accordance with the invention conform to the general formula

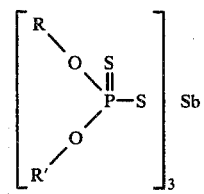

wherein R and R' can be the same or different and are hydrocarbyl radicals containing from 1 to 18 carbon atoms.

The R and R' moieties are derived from hydroxyl components such as mono-, and polyhydroxy-substituted hydrocarbons. Preferably, R and R' are derived from monohydroxy-substituted compounds containing 1 to 12 carbon atoms. Useful compounds include aromatic, cycloaliphatic, aliphatic, and branched-chain phenols and alcohols. Phenols, cyclohexanols, n-decanol, n-propanol, and isopropanol are useful.

The antimony salts can be called "antimony dihydrocarbylphosphorodithioates", "antimony tris(0,0-dihydrocarbyl)phosphorodithioates", and "antimony dihydrocarbyldithiophosphates".

The antimony hydrocarbylphosphorodithioate salts of this invention are produced via the reaction of hydrocarbylphosphorodithioic acids or their chemical equivalents with antimony compounds. Chemical equivalents for the acids include their salts with alkali metals, such as sodium and potassium.

The hydrocarbylphosphorodithioic acid reactant can be produced by a variety of methods. One method for producing the acid intermediate is the reaction of an alcohol with a phosphorus sulfide. When the intermediate is synthesized from a monoalcohol and diphosphorus pentasulfide, for example, the reaction conforms to the following equation:

$$4ROH + P_2S_5 \rightarrow 2(RO)_2PSSH + H_2S$$

Preferably, a molar excess of the alcohol reactant is used.

Use of $P_2S_5$ that has been purified by distillation is preferred because the antimony compound from it is more stable against thermal decomposition.

The hydrocarbylphosphorodithioic acid is reacted with one or more of a large group of antimony-containing compounds. Suitable antimony compounds conform to the general formula $$Sb_mX_n$$

wherein X is —O, —OH, —OOCR", —Cl, —Br, or —F; R" is an organic radical containing 1 to 12 carbon atoms; and m and n are independent and represent numbers from 1 to 5. The oxides, hydroxides, acetates, and chlorides of antimony are among the useful compounds. Preferred compounds include the oxides and hydroxides of antimony.

The antimony compound can be added to the acid intermediate alone or in admixture with an inert hydrocarbon carrier.

Normally, the acid is added to the compound, preferably suspended in a hydrocarbon carrier, at a controlled rate, so that the temperature, which increases because of the exothermic reaction, is not permitted to exceed about 50° C. For convenience, the initial portion of antimony compound will be at least half of the total to be used. It is preferred that the amount of antimony initially taken be between about 90% and 99% of the stoichiometric amount. Optionally, the initial reaction of acid and antimony compound can be carried out by adding the antimony compound to a quantity of the acid already in place in the reactor.

Subsequent additions of the antimony compound will consist of small portions. Usually, these subsequent portions will be increments containing minor amounts of antimony. Their antimony contents will be sufficient to effect at least incremental changes in the acidity of the solutions without causing significant increases in reactor temperature. While it is not essential that these subsequent increments contain equal amounts of antimony, it is preferred that they be substantially the same quantitatively.

An excess of antimony reagent should be added to the reactor in order to insure that complete neutralization has taken place.

The quantity of antimony compound added via any of the subsequent additions, i.e., the quantity in any increment added after the initial addition, will be between 0.01 and 10% of the stoichiometrically required amount of antimony. Preferably, the subsequent increments will each contain about 0.1 to 1% of the stoichiometric amount.

The timing of the incremental additions is such that the reaction can be controlled and visually inspected prior to further additions. Usually, the interval between additions will be between 10 and 100 minutes. Preferably, intervals of about 15 to 45 minutes are employed.

The attainment of a complete neutralization of the acid intermediate is detectable in various ways. These include color changes and the cessation of the evolution of condensation by-products, e.g., water.

The reaction of the antimony compound with the acid intermediate is preferably carried out under controlled conditions. It has been found that the incremental addition of the antimony reagent helps control reaction parameters such as the temperature in the reaction vessel. Since the reaction is exothermic, it is preferred that the temperature be kept below 50° C. via incremental additions of antimony or other suitable means.

Following the reaction of the antimony compound with the acid intermediate, any excess antimony reagent can be separated from the salt produced via conventional methods. Filtration is one useful separation technique.

TYPICAL PRODUCTION SCHEME

A typical scheme for carrying out the invention can be described as follows:

About 97% of the total quantity of antimony trioxide in kerosene is added to the reactor. 100% of the total organophosphorodithioic acid reactant is added thereto while maintaining the reactor at temperatures of 43° C. or below. The resultant solution is green.

Increments of antimony oxide containing about 0.5% of the stoichiometric quantity are added to the reactor at half-hour intervals. As the increments are added, the color of the solution changes from green to yellow, indicating the progress of the neutralization. When a light yellow color occurs and is maintained, the reaction is complete. Water of condensation is removed from the reactor. The product is then cooled and filtered using conventional filters, such as Cuno or Sparkler filters.

EXAMPLE I 750 gallons (about 7,250 lb) of di-n-propyl phosphorodithioic acid was added at the rate of 3 gallons per minute to 1,450 lb of about 1 micron size antimony trioxide suspended in about 1800 lb of kerosene. The resultant material was green. Antimony trioxide was added thereto at a rate of 2 lb every 30 minutes (about 0.07 lb/min) until the solution was yellow, indicating complete reaction. After removal of water by partial vacuum, the entire product was filtered using a Cuno filter in 1 hour, producing a clear solution.

EXAMPLE II (Comparison)

To 1460 lb of kerosene, 1150 lb of powdered antimony oxide, of the same particle size as that used in Example I, were added. 5500 lb of di-n-propylphosphorodithioic acid were added at a rate of 1.5 gal/min. Water formed in the reaction was removed by purging with nitrogen at 65° C. under partial vacuum. Passage through a Sparkler filter left a hazy product. Consequently, 25 lb of filter aid were added to the product and the mixture was circulated through the filter for 2 days, finally producing a filtrate that possessed only a slight haze.

The antimony salts produced in accordance with the invention can be employed as passivation agents in catalytic cracking systems. Systems in which they are operable include those disclosed in U.S. Pat. Nos. 4,031,002 and 4,166,806. The disclosures of these patents are incorporated herein by reference.

Reasonable variations can be made in the invention without departing from the scope thereof.

We claim:

1. A process of reacting one or more antimony reagents of the general formula $Sb_mX_n$; wherein X is —O, —OH, —OOCR", —Cl, —Br, or —F; R" is an organic radical containing 1 to 12 carbon atoms; and m and n are independent and represent numbers from 1 to 5, with at least one hydrocarbyl phosphorodithioic acid component to produce antimony dihydrocarbylphosphorodithioates comprising the steps of
    (a) adding less than the stoichiometric amount of antimony reagent to the acid component,
    (b) allowing the added antimony reagent to react with the acid component,
    (c) repeating steps (a) and (b) until substantially all of the acid component is neutralized, and (d) separating the desired antimony salt from the product of step (c).

2. The process of claim 1 wherein the antimony reagent is antimony trioxide.

3. The process of claim 2 wherein the acid component contains a dialkyl phosphorodithioic acid.

4. The process of claim 3 wherein the acid component is di-n-propylphosphorodithioic acid.

* * * * *